United States Patent [19]

Strehler et al.

[11] 4,165,335
[45] Aug. 21, 1979

[54] SALTS OF DICARBOXYLIC ACIDS AND DIAMINES, HAVING AN IMPROVED COLOR NUMBER, THEIR MANUFACTURE AND THEIR USE

[75] Inventors: Hugo Strehler, Frankenthal; Ernst Dietl, Ludwigshafen; Georg Pilz, Neustadt, all of Fed. Rep. of Germany

[73] Assignee: BASF Aktiengesellschaft, Fed. Rep. of Germany

[21] Appl. No.: 810,273

[22] Filed: Jun. 27, 1977

[30] Foreign Application Priority Data

Jul. 23, 1976 [DE] Fed. Rep. of Germany ..... 2633110

[51] Int. Cl.² .................. C07C 109/087; C07C 87/14
[52] U.S. Cl. ................................ 260/501.2; 528/336; 525/6
[58] Field of Search ...................... 260/501.2; 528/336; 526/6

[56] References Cited

U.S. PATENT DOCUMENTS

| | | | |
|---|---|---|---|
| 2,130,947 | 9/1938 | Carothers | 260/501.2 |
| 2,512,632 | 6/1950 | Fisher et al. | 528/336 |
| 3,439,025 | 4/1969 | Gallay et al. | 260/501.2 |
| 3,661,982 | 5/1972 | Beswick | 260/501.2 |
| 3,825,586 | 7/1974 | Traumann | 260/501.2 |
| 3,944,598 | 3/1976 | Paustian et al. | 260/501.2 |

FOREIGN PATENT DOCUMENTS

45-849  12/1970  Japan ..................................... 260/501.2

*Primary Examiner*—Bernard Helfin
*Assistant Examiner*—G. T. Breitenstein
*Attorney, Agent, or Firm*—Keil & Witherspoon

[57] ABSTRACT

Salts of alkanedicarboxylic acids of 4 to 12 carbon atoms and diamines of the formula $H_2N-R-NH_2$, where R is alkylene of 2 to 12 carbon atoms or is a radical of the formula

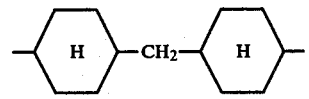

or

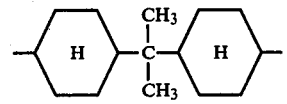

which contain hydrazine hydrate, the manufacture of the salts in solution, and their use for the manufacture of nylons.

5 Claims, No Drawings

SALTS OF DICARBOXYLIC ACIDS AND DIAMINES, HAVING AN IMPROVED COLOR NUMBER, THEIR MANUFACTURE AND THEIR USE

The invention relates to salts of alkanedicarboxylic acids of 4 to 12 carbon atoms and diamines, having an improved color number, to a process for their manufacture, and to their use.

Salts of dicarboxylic acids and diamines, e.g. hexamethylenediammonium adipate, are manufactured on a large scale and are used as starting materials for the manufacture of nylons by polycondensation. Such nylons have to conform to very high standards as regards intrinsic color. The same is true of the salts of dicarboxylic acids and diamines, used as starting materials. Even though great care is already being devoted to the purification of the starting material, e.g. by crystallization or distillation, the color of the salts produced therefrom still requires improvement. This is also true of other characteristics, e.g. the periodate number and the UV number of the salts produced. The adverse properties are attributable to very small amounts of impurities of a hitherto unknown nature, which it has not been possible to remove, at acceptable expense, by the conventional methods of purification. The shortcomings of the salts of dicarboxylic acids and diamines accordingly apply to the nylons produced therefrom, because of the high quality standards demanded of such nylons.

It is an object of the present invention to provide salts of dicarboxylic acids and diamines which conform more closely to the required standards of color number, yellowness index, periodate number and UV-number and which permit the manufacture of nylons of improved quality.

We have found that this object is achieved by providing salts of alkanedicarboxylic acids of 4 to 12 carbon atoms and diamines of the formula $H_2N-R-NH_2$, where R is alkylene of 2 to 12 carbon atoms or is a radical of the formula

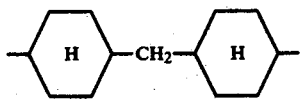

or

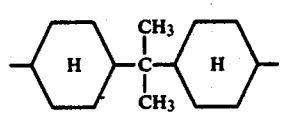

which contain hydrazine hydrate.

Further, we have found that salts of alkanedicarboxylic acids of 4 to 12 carbon atoms and diamines of the formula $H_2N-R-NH_2$, where R is alkylene of 2 to 12 carbon atoms or is a radical of the formula

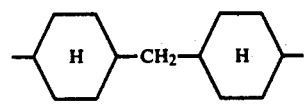

or

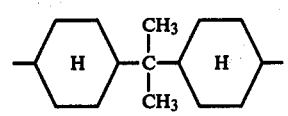

having an improved color number, may be obtained advantageously by reaction of alkanedicarboxylic acids of 4 to 12 carbon atoms and diamines of the formula $H_2N-R-NH_2$, where R is alkylene of 2 to 12 carbon atoms or is a radical of the formula

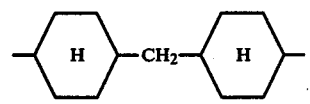

or

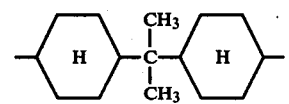

in solution, if hydrazine hydrate is added to the dicarboxylic acids and/or diamines used as starting compounds.

The present invention further relates to the use of salts of alkanedicarboxylic acids of 4 to 12 carbon atoms and diamines of the formula $H_2N-R-NH_2$, where R is alkylene of 2 to 12 carbon atoms or is a radical of the formula

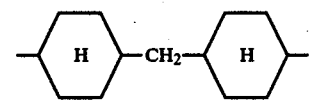

or

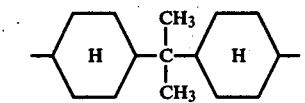

which contain hydrazine hydrate, for the manufacture of nylons.

The salts of dicarboxylic acids and diamines obtained by the process of the invention have the advantage that their color number, yellowness index, periodate number and UV-number has been improved by a simple method. Accordingly, the said salts are superior to conventional salts of the same type for the manufacture of nylons.

The invention is based on the concept of adding, in the course of the manufacture of salts of dicarboxylic acids and diamines, such as are used to manufacture nylons by condensation, small amounts of reducing compounds, e.g. hydrazine hydrate or its derivatives, which leave no residue on ashing and which do not interfere with the polycondensation.

The starting materials used are alkanedicarboxylic acids of 4 to 12 carbon atoms. α,ω-Alkanedicarboxylic acids, especially those with a straight carbon chain, are preferred. Those of 6 to 12 carbon atoms are particularly preferred, and adipic acid and sebacic acid are industrially of especial importance. Examples of suitable dicarboxylic acids are glutaric acid, adipic acid, suberic acid, sebacic acid or dodecanedicarboxylic acid.

The diamines used have the formula H₂N—R—NH₂, where R is alkylene of 2 to 12 carbon atoms or is a radical of the formula

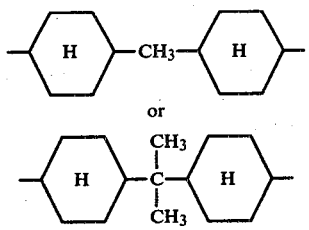

In particular, alkanediamines of 4 to 12 carbon atoms are used. Preferred diamines are α,ω-alkanediamines, especially those with a straight carbon chain. Alkanediamines of 6 to 12 carbon atoms are particularly preferred, And hexamethylenediamine has attained especial importance. Examples of suitable alkanediamines are hexamethylenediamine, heptamethylenediamine, octamethylenediamine, decamethylenediamine, dodecanemethylenediamine, tetramethylenediamine, bis-(4-aminocyclohexyl)-methane or 2,2-bis-(4-aminocyclohexyl)-propane.

It will be obvious from the foregoing that hexamethylenediammonium adipate and hexamethylenediammonium sebacate are preferred end products.

Salts of the said diamines and dicarboxylic acids are as a rule prepared in solution, e.g. in water, methanol or ethanol, but especially in aqueous solution. For example, aqueous solutions of dicarboxylic acids of more than 40% strength by weight, and especially more than 50% strength by weight, are used as starting materials. It is particularly advantageous to use aqueous solutions which are virtually saturated. Such aqueous solutions are then reacted with the fused diamines. It is also possible to use aqueous solutions of diamines, preferably of more than 50% strength by weight, and to react such solutions with solid alkanedicarboxylic acids. As a rule, a temperature of from 20° to 100° C., especially from 60° to 90° C., is maintained during the reaction. In view of the use of the products for polycondensation, the dicarboxylic acids and diamines are of course employed in stoichiometric amounts.

Aqueous solutions, of, for example, from 50 to 60% strength by weight, of the corresponding salts of dicarboxylic acids and diamines are thus obtained. From the aqueous solutions, the corresponding salts are themselves obtained by, for example, evaporating and/or cooling. However, it is also possible to use the aqueous solutions, as obtained from their process of manufacture, directly for the manufacture of nylons. Accordingly, the term salts of dicarboxylic acids and diamines is to be taken also to include aqueous solutions which contain such salts and are suitable for the manufacture of nylons.

It is an essential feature of the invention that hydrazine hydrate is added to the starting materials, i.e. the dicarboxylic acids and/or diamines. Advantageously, hydrazine hydrate is added to the liquid starting materials, e.g. to the aqueous solutions of dicarboxylic acids or diamines, or to the fused diamines.

The addition of hydrazine hydrate to the fused diamines has proved particularly advantageous. Preferably, from 5 to 100 ppm of hydrazine hydrate are added, and the addition of from 10 to 50 ppm has proved particularly advantageous; the said amounts of hydrazine hydrate are in each case based on the diamines used. Obviously, the salts obtained from the alkanedicarboxylic acids and diamines contain hydrazine hydrate in the stated amounts. The form in which hydrazine hydrate is present in the salts obtained is not known.

Polycondensation of the salts, or aqueous solutions, thus obtained gives the corresponding nylons. The polycondensation is carried out by, for example, heating the salts or the aqueous solution to from 150° to 220° C., removing the resulting water and then polycondensing the resulting melt at from 220° to 275° C., under atmospheric or reduced pressure. Suitable processes are described in, for example, Klare, Synthetische Fasern aus Polyamiden, Akademie Verlag, or British Patent Specification No. 674,954. The nylons can be used for the production of shaped articles, e.g. fibers, moldings, films and coatings.

The Examples which follow illustrate the process of the invention.

EXAMPLES

The dicarboxylic acid, in the form of a 50% strength by weight aqueous solution, is reacted, at 95° C., with fused diamine which contains hydrazine hydrate. The results achieved with various dicarboxylic acids and diamines, and with varying amounts of hydrazine hydrate, are listed in the Table which follows:

TABLE

| Example | Salt from | Hydrazine hydrate ppm | Intrinsic color[1] at 90° C. | Yellowing[2] | UV number[3] | Periodate number[4] |
|---|---|---|---|---|---|---|
| 1 | Adipic acid and | — | 3 | 20 | 109 | 0.026 |
|   | Hexamethylenediamine | 10 | 3 | 12 | 52 | 0.024 |
| 2 | Adipic acid and Hexamethylenediamine | 40 | 3 | 7 | 47 | 0.013 |
| 3 | Adipic acid and Hexamethylenediamine | 50 | 2 | 6 | 32 | 0.005 |
| 4 | Sebacic acid and | — | 92 | 149 | 2,200 | 0.228 |
|   | Hexamethylenediamine | 40 | 41 | 88 | 1,015 | 0.124 |
| 5 | Adipic acid and | — | 5 | 5 | 52 | 0.003 |
|   | Propylenediamine | 50 | 3 | 5 | 38 | 0.002 |
| 6 | Adipic acid and | — | 68 | 117 | 3,300 | 0.189 |
|   | Tetramethylenediamine | 50 | 44 | 95 | 3,100 | 0.152 |
| 7 | Adipic acid and | — | 12 | 23 | — | 0.043 |
|   | Octamethylenediamine | 50 | 10 | 13 | — | 0.022 |
| 8 | Adipic acid and | — | 111 | 242 | 12,900 | 1.000 |
|   | Bis-(4-aminocyclohexyl)-methane | 50 | 73 | 199 | 12,600 | 0.580 |
| 9 | Adipic acid and | — | 72 | 123 | 7,500 | 0.205 |

TABLE-continued

| Example | Salt from | Hydrazine hydrate ppm | Intrinsic color[1] at 90° C. | Yellowing[2] | UV number[3] | Periodate number[4] |
|---|---|---|---|---|---|---|
| | 2,2-Bis-(4-aminocyclohexyl)-propane | 50 | 59 | 115 | 6,500 | 0.140 |

The salts obtained can be readily converted into nylons by the method of British Patent Specification 674,954.
[1]Intrinsic color: APHA value, measured at 90° C. on a 40% strength by weight aqueous solution.
[2]Yellowing: APHA value, measured on a 40% strength by weight aqueous solution after 24 hours' heating at 85° C. The extinction is determined by means of an Elko II photometer with S 47 and J 62 filters, for a 5 cm thick layer. The APHA value is calculated, by means of a calibration curve, from the extinction with the S 47 filter minus the extinction with the J 62 filter.
[3]UV number: 100 × the sum of the extinctions at 266, 282 and 295 mμ × 100, measured on a 10 cm thick layer of a 40% strength by weight aqueous solution at 25° C., against doubly distilled water. [4]Periodate number: 1 ml of an 0.5% strength by weight aqueous potassium periodate solution is added to 50 g of a 40% strength by weight aqueous solution of the salt. The mixture is heated for 30 minutes at 90° C. and is then cooled to room temperature, and the extinction of a 5 cm thick layer is measured with an Elko II photometer, using an S 45 filter.

We claim:

1. Salts of alkanedicarboxylic acids of 4 to 12 carbon atoms and diamines of the formula $H_2N-R-NH_2$, where R is alkylene of 2 to 12 carbon atoms or is a radical of the formula

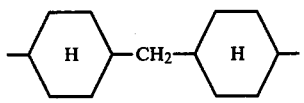

or

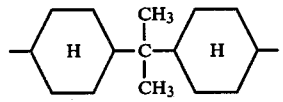

which contain up to 100 ppm of hydrazine hydrate to improve the color number, yellowness index, periodate number and UV-number of the salts.

2. Hexamethylenediammonium adipate which contains up to 100 ppm of hydrazine hydrate to improve the color number, yellowness index, periodate number and UV-number of the hexamethylenediammonium adipate.

3. Hexamethylenediammonium sebacate which contains up to 100 ppm of hydrazine hydrate to improve the color number, yellowness index, periodate number and UV-number of the hexamethylenediammonium sebacate.

4. Salts as set forth in claim 1, wherein the amount of hydrazine hydrate is from 5 to 100 ppm.

5. Salts as set forth in claim 1, wherein the amount of hydrazine hydrate is from 10 to 50 ppm.

* * * * *